US012721929B2

(12) United States Patent
Park

(10) Patent No.: US 12,721,929 B2
(45) Date of Patent: Sep. 1, 2026

(54) COMPOSITION USING FIBROTIC ACELLULAR DERMAL MATRIX, AND METHOD FOR PREPARING SAME

(71) Applicant: CG BIO CO., LTD., Seoul (KR)

(72) Inventor: Heejun Park, Seoul (KR)

(73) Assignee: CG BIO CO., LTD., Seoul (KR)

( * ) Notice: Subject to any disclaimer, the term of this patent is extended or adjusted under 35 U.S.C. 154(b) by 300 days.

(21) Appl. No.: 18/576,591

(22) PCT Filed: Jul. 5, 2022

(86) PCT No.: PCT/KR2022/009692
§ 371 (c)(1),
(2) Date: Jan. 4, 2024

(87) PCT Pub. No.: WO2023/282593
PCT Pub. Date: Jan. 12, 2023

(65) Prior Publication Data

US 2024/0285828 A1 Aug. 29, 2024

(30) Foreign Application Priority Data

Jul. 7, 2021 (KR) ........................ 10-2021-0089043

(51) Int. Cl.
*A61L 27/36* (2006.01)
*A61L 27/38* (2006.01)
*A61L 27/54* (2006.01)

(52) U.S. Cl.
CPC ......... *A61L 27/362* (2013.01); *A61L 27/3691* (2013.01); *A61L 27/3834* (2013.01); *A61L 27/54* (2013.01); *A61L 2300/414* (2013.01)

(58) Field of Classification Search
CPC ............... A61L 27/362; A61L 27/3834; A61L 27/3691; A61L 27/54; A61L 2430/34; A61L 2300/414; A61K 9/70; A61K 35/36; A61P 17/02; C12N 5/0629
See application file for complete search history.

(56) References Cited

U.S. PATENT DOCUMENTS 6,933,326 B1 * 8/2005 Griffey ................. A61L 31/005 523/113
2010/0272782 A1 10/2010 Owens et al.
2013/0158658 A1 6/2013 Hayzlett

FOREIGN PATENT DOCUMENTS

KR 10-2016-0049459 A 5/2016
KR 10-2020-0008602 A 1/2020
WO 03/007790 A2 1/2003
(Continued)

OTHER PUBLICATIONS

WIPO/ISA/KR, "International Search Report and Written Opinion" issued on Oct. 5, 2022 in PCT/KR2022/009692, 7 pages.
(Continued)

*Primary Examiner* — Hong Yu
(74) *Attorney, Agent, or Firm* — J. Peter Paredes; Amin Wasserman Gurnani LLP

(57) ABSTRACT

The present invention relates to a composition using a fiberized acellular dermal matrix and a method of preparing the same and, more particularly, to a composition using a fiberized acellular dermal matrix prepared without addition of a biocompatible polymer and a method of preparing the same.

9 Claims, 3 Drawing Sheets

(56) References Cited

FOREIGN PATENT DOCUMENTS

WO 2009/009620 A2 1/2009

OTHER PUBLICATIONS

Bottino, M.C., et al. "Acellular dermal matrix graft: Synergistic effect of rehydration and natural crosslinking on mechanical properties", J. Biomed. Mater. Res., 95B: 276-282 (2010).

European Patent Office, European Search Report dated Sep. 26, 2025 issued in corresponding EP patent application No. EP22837945.9, 11 pages.

* cited by examiner

【FIG. 1】
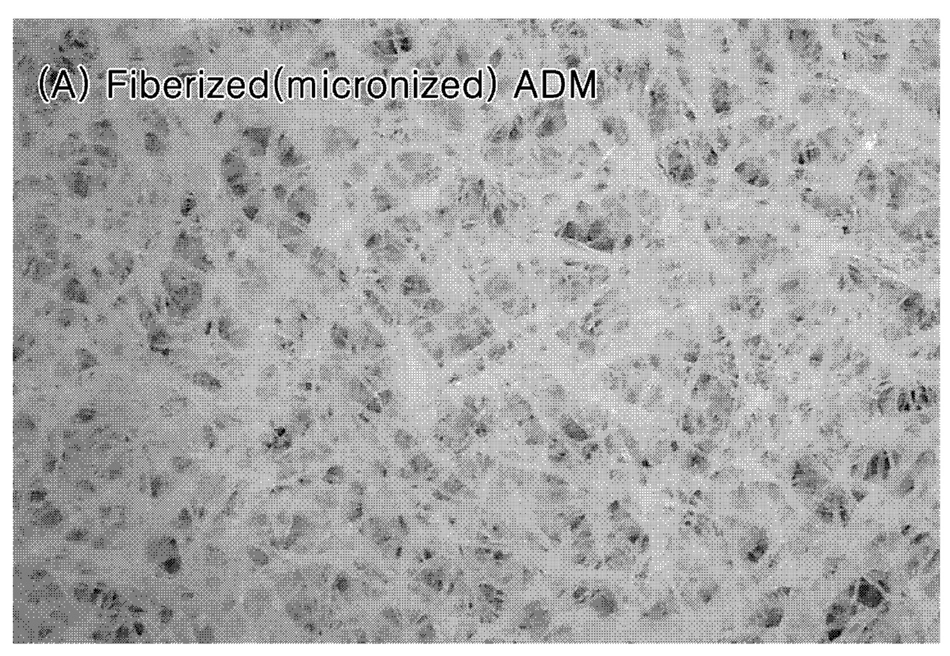
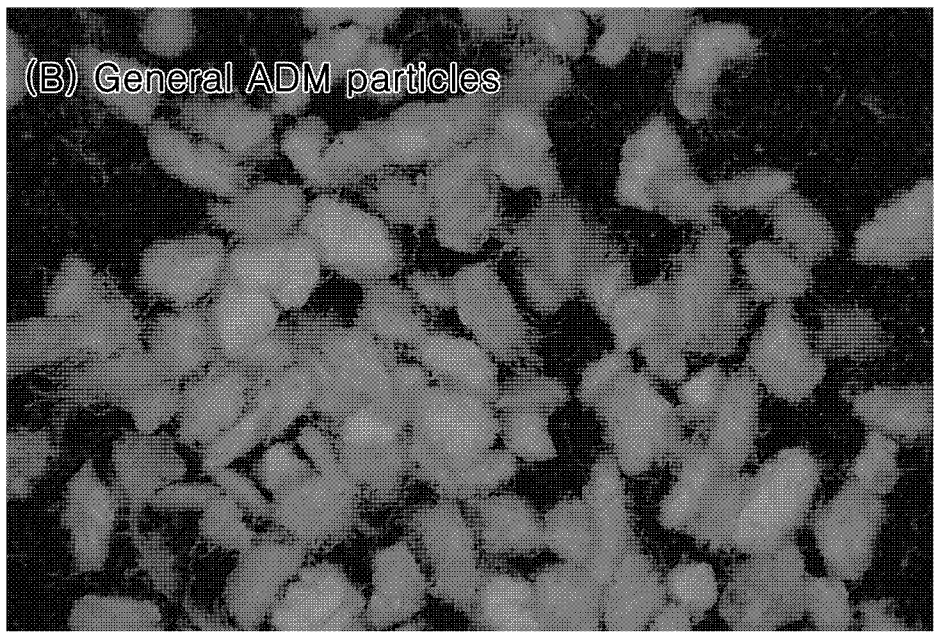

【FIG. 2】
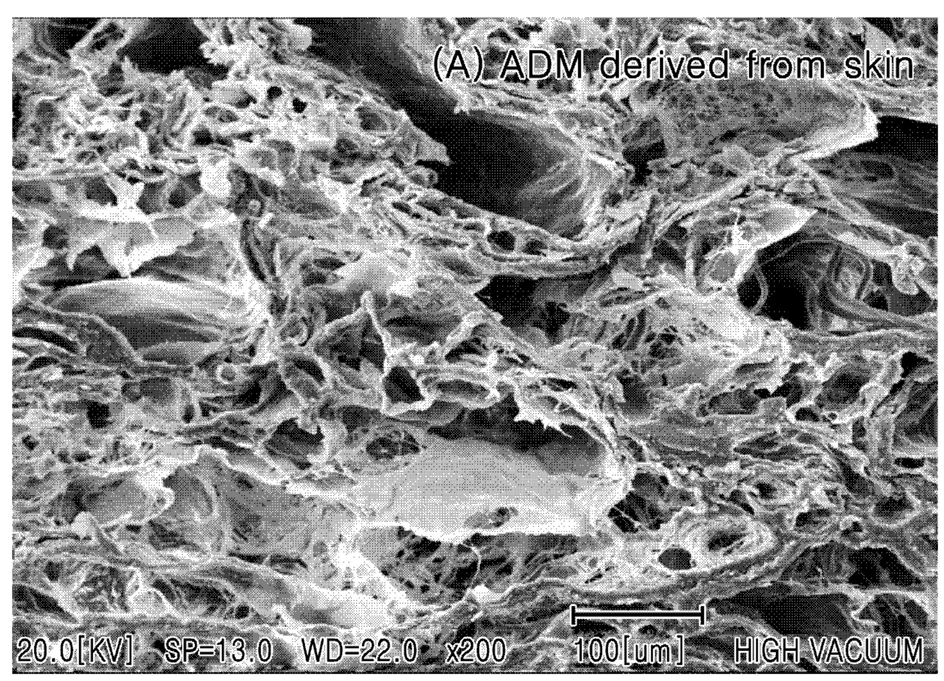
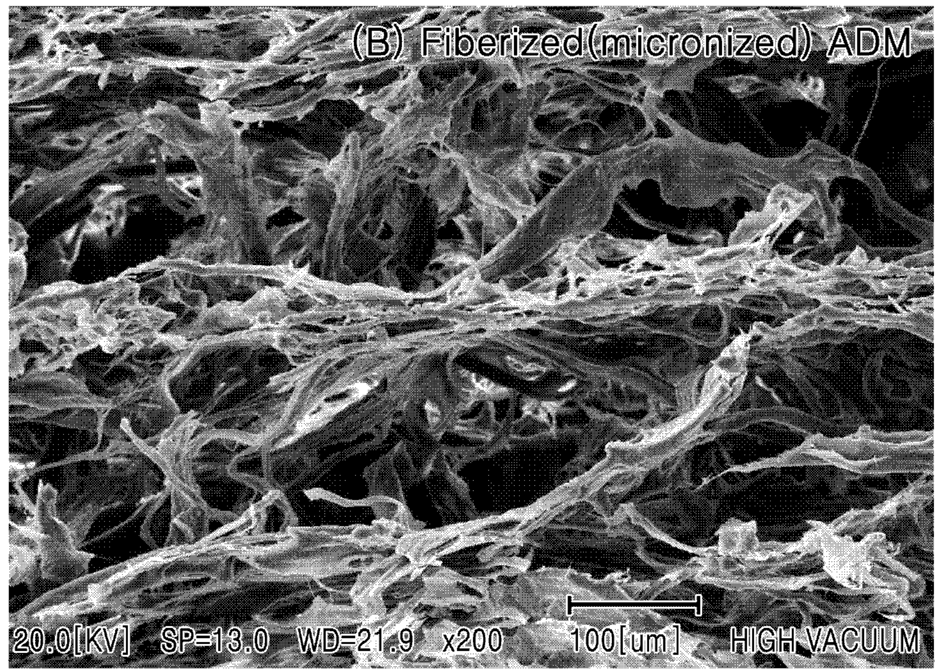

【FIG. 3】
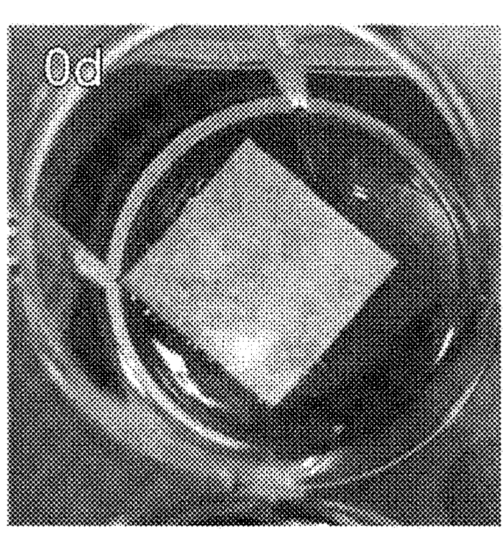
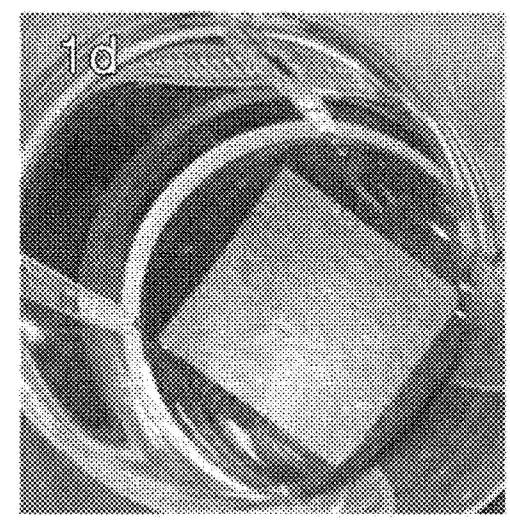
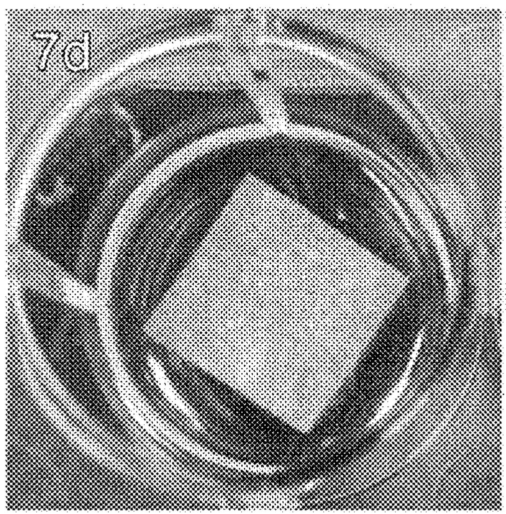

COMPOSITION USING FIBROTIC ACELLULAR DERMAL MATRIX, AND METHOD FOR PREPARING SAME

TECHNICAL FIELD

The present invention relates to a composition using a fiberized acellular dermal matrix and a method of preparing the same and, more particularly, to a composition using a fiberized acellular dermal matrix prepared without addition of a biocompatible polymer and a method of preparing the same.

BACKGROUND ART

A wound is a break or tear in the skin or other tissue caused by external pressure that involves a break in the continuity of the tissue, and generally refers to an opening in the skin caused by damage to the dermis layer of the skin. Wound surgery basically involves stitching and dressing a wound to block exposure to an external environment so as to prevent infection and suppress inflammatory response.

Materials used in wound dressing may be roughly classified into homologous skin and heterologous skin. A wound dressing material may be prepared by extracting a specific polymer from these materials or using a dermal matrix.

An acellular dermal matrix (ADM) is a biocompatible material prepared by removing the epidermis from donated cadaveric skin tissue to eliminate immune rejection, followed by decellularization of the dermis, and is widely used in soft tissue reconstruction in the field of tissue engineering, as well as in allografts for burn treatment. Dermal tissue is composed of 80% to 90% collagen, elastin, and glycosaminoglycan.

An acellular dermal matrix (ADM) prepared by decellularization and freeze-drying of skin tissue from cadavers was commercialized under the tradename AlloDerm (allograft) by LifeCell Corporation in 1994 to be used for burn treatment and skin reconstruction. AlloDerm (allograft) is safer than heterologous products and shows significantly better engraftment and therapeutic effects. Similar products include Bard Dabol's AlloMax, which is used as a graft, and Ethicon's FlexHD, which has increased adhesion.

However, such sheet-type acellular dermal matrix dressings as described above are difficult to use for wounds in irregular or recessed areas and are less efficient due to the necessity of cutting a tissue sheet or attaching multiple sheets together before use depending on the size and shape of a wound site.

In response, LifeCell Corporation applied for a patent for a technology that micronizes an acellular dermal matrix (U.S. Pat. No. 6,933,326B1) in 1999, applied for a patent for a composition composed of a mixture of a micronized acellular dermal matrix and an acidic solution (U.S. Pat. No. 9,382,422B2) in 2008, and launched an injectable micronized form of AlloDerm (Cymetra). In addition, Wright Medical Group developed Graftjacket, a sheet-type acellular dermal matrix product, in injectable form and launched Graftjacket Xpress.

In addition, L&C Bio, a Korean company, applied for a patent for a composition prepared by micronizing an acellular dermal matrix, followed by crosslinking with hyaluronic acid (KR10-1523878B1) in 2014.

However, such a composition prepared by crosslinking of acellular dermal matrix particles with a biocompatible polymer as described above is insufficient as a wound dressing material, despite being suitable for use as fillers or implants due to high structural stability and good properties in terms of degree of crosslinking, viscoelasticity, curability, and extrudability. That is, the micronized acellular dermal matrix is in liquid form and thus is likely to leak out of a dressing rather than being secured in a wound site, making even distribution over a wound difficult.

In response, the applicant, CGBIO Co., Ltd., has applied for a patent for a composition including a fiberized acellular dermal matrix and a biocompatible polymer and a method of preparing the same (KR10-2019-7037462). The invention of this application was conceived to solve problems of conventional compositions as described above and provided a composition that has smooth applicability and good adhesion while exhibiting good structural stability due to the presence of a polymer, thereby ensuring good shape retention and improved therapeutic effects, and a method of preparing the same.

However, in the invention of the prior application as described above, preparation of the composition requires a process of dissolving a biocompatible polymer, such as gelatin, hyaluronic acid, collagen, poloxamer, or the like, in hot water at 50° C. to 70° C. so as to mix the biocompatible polymer with an acellular dermal matrix. In addition, in the case of using gelatin as the biocompatible polymer, a process of heat treatment at about 60° C. is additionally required prior to radiation sterilization to prevent property changes such as hardening of the composition due to crosslinking with gelatin during radiation sterilization of the mixture, thereby causing increased process complexity and additional costs related therewith.

Accordingly, the inventors of the present invention have completed the present invention to provide a composition using a fiberized acellular dermal matrix, which does not undergo property changes due to heat during sterilization by omitting addition of a polymer, does not require additional processes, such as mixing of a polymer therewith and heat treatment for prevention of property changes, can be prepared in the form of a soft sheet to be uniformly applied to a wound regardless of the irregularity, size, and shape of the site of the wound, and has high structural stability and good shape retention due to use of a fiberized acellular dermal matrix with a long major axis length, and a method of preparing the same.

DISCLOSURE

Technical Problem

It is one aspect of the present invention to provide a composition using a fiberized acellular dermal matrix, which has good flexibility and thus can be applied to any wound site regardless of the irregularity, size, and shape thereof, and a method of preparing the same.

It is another aspect of the present invention to provide a composition using a fiberized acellular dermal matrix, which can be prepared in sheet form due to high structural stability thereof and can be uniformly applied to a wound site without flowing down therefrom, and a method of preparing the same.

It is a further aspect of the present invention to provide a composition using a fiberized acellular dermal matrix, which can avoid property changes due to heat by omitting addition of a biocompatible polymer, and can enable process simplification and cost reduction by eliminating the need for an additional process associated with unique properties of the biocompatible polymer, and a method of preparing the same.

Technical Solution

In accordance with one aspect of the present invention, there is provided a method of preparing a composition using a fiberized acellular dermal matrix, including:

(a) preparing a fiberized acellular dermal matrix by pulverizing an acellular dermal matrix;

(b) preparing a rehydrated fiberized acellular dermal matrix by adding water to the fiberized acellular dermal matrix;

(c) separating the rehydrated fiberized acellular dermal matrix based on a major axis length thereof; and (d) drying the separated rehydrated fiberized acellular dermal matrix.

Preferably, the step (c) may include spreading the rehydrated fiberized acellular dermal matrix on a mesh, followed by discharging a fiberized acellular dermal matrix having a major axis length shorter than a sieve size of the mesh through the mesh along with water.

More preferably, the step (d) may include drying the rehydrated fiberized acellular dermal matrix remaining on the mesh.

Preferably, the method may further include: before the step (c), adding water to the mesh in an amount three or more times a volume by weight of the rehydrated fiberized acellular dermal matrix such that the fiberized acellular dermal matrix is evenly distributed.

Preferably, the step (c) may include spreading the rehydrated fiberized acellular dermal matrix on the mesh, followed by discharging a fiberized acellular dermal matrix having a major axis length of less than 100 μm through the mesh along with water.

Preferably, the step (c) may include separating the fiberized acellular dermal matrix such that 90% or more of the separated fiberized acellular dermal matrix has a major axis length of 100 μm to 2,000 μm.

Preferably, the step (c) may include separating the fiberized acellular dermal matrix such that 50% to 90% or more of the separated fiberized acellular dermal matrix has a major axis length of 600 μm to 800 μm.

Preferably, the method may further include: processing the dried fiberized acellular dermal matrix into sheet form.

Preferably, the method may further include: crosslinking the fiberized acellular dermal matrix.

In accordance with another aspect of the present invention, there is provided a composition using a fiberized acellular dermal matrix, including: a fiberized acellular dermal matrix; and water, wherein 90% or more of the fiberized acellular dermal matrix has a major axis length of 100 μm to 2,000 μm, and the composition is prepared without addition of a biocompatible polymer.

Preferably, 50% to 90% of the fiberized acellular dermal matrix may have a major axis length of 600 μm to 800 μm.

Preferably, the fiberized acellular dermal matrix may be prepared using acellular dermis derived from skin.

Preferably, the water may be present in an amount of 0.5 wt % to 20 wt % in the composition.

Preferably, the composition may further include: at least one selected from among pharmaceutically acceptable antimicrobial agents, excipients, and additives.

Preferably, the composition may further include: at least one selected from among a stem cell and a growth factor.

Preferably, the composition may be subjected to a crosslinking process to have a crosslinked structure.

Preferably, the composition may be of a sheet type.

Advantageous Effects

The method of preparing a composition using a fiberized acellular dermal matrix according to the present invention can prevent heat-induced property changes in the composition by omitting addition of a biocompatible polymer, can reduce the number of preparation steps by eliminating the need for a process of dissolving the polymer in high-temperature water and mixing the dissolved polymer with the fiberized acellular dermal matrix and a process of heat treatment of the mixture of the fiberized acellular dermal matrix and the polymer, and can reduce preparation costs by eliminating the need for additional equipment and manpower for heat treatment.

In addition, since the fiberized acellular dermal matrix can form a network structure by spreading the composition on a mesh or a filter, the composition can be prepared in sheet form without addition of a biocompatible polymer.

The composition according to the present invention is soft due to omission of a polymer and thus can be easily applied to wounds in areas which make application of a conventional composition difficult due to the irregularity, size, or shape thereof.

In addition, since the composition according to the present invention has a network structure without addition of a polymer by using the fiberized acellular dermal matrix, that is, an acellular dermal matrix having a large major axis length, the composition can have high structural stability and can be prepared in the form of a sheet-type wound dressing to be uniformly applied to a wound site without flowing down therefrom, thereby ensuring improved therapeutic effects.

In particular, the composition according to the present invention has a very similar structure to a dermal matrix at a wound site in the human body by omitting addition of a polymer, and thus has good properties in terms of bioadhesion and in-vivo integrity, and maintains a moist environment well, thereby providing good therapeutic effects.

In addition, the composition according to the present invention has good shape retention during specialized procedures due to high stability after prolonged rehydration, and can be prepared into sheet form having various widths, lengths, and thicknesses depending on the type of wound site or the nature of surgery, thereby ensuring improved treatment of wounds.

DESCRIPTION OF DRAWINGS

FIG. 1 shows comparison of a fiberized acellular dermal matrix (A) having a network structure according to the present invention with a non-fiberized particulate acellular dermal matrix (B).

FIG. 2 shows comparison in structure between an acellular dermal matrix derived from human skin (A) and a composition (B) using a fiberized acellular dermal matrix according to the present invention.

FIG. 3 shows experimental results demonstrating that a sheet-type composition according to the present invention retains a shape thereof even after prolonged rehydration.

BEST MODE

Hereinafter, embodiments of the present invention will be described in detail. Some specific details that can be readily recognized and conceived by those skilled in the field to which the present invention pertains or in similar fields thereto will be omitted from the description herein.

In accordance with one aspect of the present invention, there is provided a method of preparing a composition using a fiberized acellular dermal matrix, including: (a) preparing a fiberized acellular dermal matrix by pulverizing an acellular dermal matrix; (b) preparing a rehydrated fiberized acellular dermal matrix by adding water to the fiberized acellular dermal matrix; and (c) separating the rehydrated fiberized acellular dermal matrix based on a major axis length thereof; and (d) drying the separated rehydrated fiberized acellular dermal matrix.

Dermal tissue according to the present invention may be bone, ligament, tendon, or skin, and may be heterologous dermal tissue or homologous dermal tissue, preferably homologous dermal tissue.

As used herein, "fiberized acellular dermal matrix" refers to a micronized acellular dermal matrix, the individual shape of which is not spherical or streamlined, but rather a long, thin fiber type like thread.

The acellular dermal matrix used in the step of preparing a fiberized acellular dermal matrix may have a thickness of 0.1 mm or more, preferably 0.3 mm or more.

A number of methods of preparing the acellular dermal matrix (ADM) are known in the art.

The acellular dermal matrix according to the present invention is in fiberized form. In the present invention, in order to prepare the fiberized acellular dermal matrix, freeze-dried skin prepared by a typical method known in the art may be pulverized into fibers using a pulverizing mill or the like. For fiberizing, preferably, the acellular dermal matrix may be pulverized into fine fibers.

Pulverization of the acellular dermal matrix may be carried out using a cutting mill, a food processor, an agate mill, a freeze mill, a micronizer, a vibratory micro mill, a jaw crusher, a mortar grinder, a planetary mill, a disk mill, a ball mill, or a variable speed rotor mill, preferably using a cutting mill.

Preferably, the cutting mill is operated under conditions of a rotational speed of 500 rpm to 2,000 rpm and a sieve size of 500 μm to 1,000 μm.

The fiberized acellular dermal matrix obtained through the above process is rehydrated by adding water thereto. Then, the rehydrated fiberized acellular dermal matrix is spread on a mesh, followed by draining water. Water used in the present invention may be sterile distilled water.

Preferably, the fiberized acellular dermal matrix may be rehydrated by adding water in an amount three or more times the volume by weight of the fiberized freeze-dried acellular dermal matrix.

The mesh may be preferably a mesh soaked with water, or may be a mesh, filter, or the like placed in a water bath. Introducing the rehydrated fiberized acellular dermal matrix onto this type of mesh may help to ensure that the rehydrated fiberized acellular dermal matrix is evenly distributed in water without being accumulated or concentrated on one side, thereby allowing sufficient rehydration of the fiberized acellular dermal matrix.

In order to ensure even distribution of the fiberized acellular dermal matrix, shaking of the water bath or stirring with a magnetic bar in the water bath may be performed.

The rehydrated fiberized acellular dermal matrix may be spread on the mesh to a thickness of 0.1 mm or more, and the mesh may have a sieve size of 100 μm to 500 μm.

Once the fiberized acellular dermal matrix is evenly distributed, by raising the mesh or by placing the fiberized acellular dermal matrix on a filter and applying pressure to the fiberized acellular dermal matrix in the direction of gravity using a vacuum pump, a fiberized acellular dermal matrix having a major axis length shorter than a sieve size of the mesh or the filter is discharged along with water, thereby filtering out a fiberized acellular dermal matrix having a major axis length of a predetermined value or greater.

For example, when the mesh has a sieve size of 100 μm, a fiberized acellular dermal matrix having a major axis length of less than 100 μm can be discharged along with water through openings of the mesh to be separated from a fiberized acellular dermal matrix having a major axis length of 100 μm or greater.

The fiberized acellular dermal matrix contained in the composition prepared by the method according to the present invention may have a major axis length of 100 μm to 3,000 μm. Preferably, 90% or more of the fiberized acellular dermal matrix has a major axis length of 100 μm to 2,000 μm. More preferably, 50% to 90% or more of the fiberized acellular dermal matrix has a major axis length of 600 μm to 800 μm.

If a fiberized acellular dermal matrix having a major axis length of less than 100 μm is present in a large proportion in the composition, when attempting to process the composition into sheet form, the composition cannot be properly formed into a sheet or can only be formed into a film, making flexible attachment to a wound site difficult.

The major axis length-dependent distribution and content of the fiberized acellular dermal matrix may be controlled by adjusting the sieve size of the mesh.

A sheet-type composition according to the present invention may be prepared by spreading the rehydrated fiberized acellular dermal matrix on the mesh surrounded by a mold or frame, followed by shaping and processing into sheet form before drying or drying before processing into sheet form.

Here, drying may be at least one of room temperature drying, freeze drying, and heat drying. In addition, drying may be carried out with the fiberized acellular dermal matrix spread on the mesh.

The sheet-type composition may have a water content of 0.5 wt % to 20 wt % after drying.

A thickness of the sheet-type composition may be controlled by adjusting the amount of the fiberized acellular dermal matrix spread on the mesh or by cutting the sheet-type composition to a desired thickness after drying.

The sheet-type composition may be prepared in various widths, lengths, and thicknesses depending on the type of wound site or the nature of surgery.

The prepared sheet-type composition may be further subjected to non-chemical crosslinking using exposure to radiation, pressure reduction, and heat, or chemical crosslinking using a crosslinking agent, depending on required properties (degree of crosslinking, degree of curing, etc.).

The composition prepared by the method according to the present invention may include 80 wt % to 99.5 wt % of the fiberized acellular dermal matrix and 0.5 wt % to 20 wt % of water.

The composition may be prepared in the form of an aqueous solution, a suspension, an emulsion, a paste, a cream, a balm, an ointment, a foam, a sheet, a gel, a gum, a spray, a slurry, a film, a granule, a patch, a powder, and the like. In particular, in a preferred embodiment of the present invention, the composition may be prepared in sheet form.

The composition may further include at least one selected from among pharmaceutically acceptable antimicrobial agents, excipients, and additives. Suitable antimicrobial agents include biocides such as short-chain alcohols, benzalkonium chloride ("BAC"), dodecyl dimethyl ammonium chloride ("DDAC"), and zeolite ("CWT-A"). Other possible antimicrobial agents include isothiazolone, alkyl dimethyl ammonium chloride, triazine, 2-thiocyanomethylthiobenzothiazole, methylene bisthiocyanate, acrolein, dodecylguanidine hydrochloride, chlorophenol, quaternary ammonium salts, glutaraldehyde, dithiocarbamate, 2-mercaptobenzothiazole, para-chloro-meta-xylenol, silver, chlorhexidine, polyhexamethylene biguanide, n-halamine, triclosan, phospholipids, α-hydroxy acids, 2,2-dibromo-3-nitrilopropionamide, 2-bromo-2-nitro-1,3-propanediol, farnesol, iodine, bromine, hydrogen peroxide, chlorine dioxide, vegetable oils, plant extracts, benzalkonium chloride, chlorine, sodium hypochlorite, or combinations thereof.

Suitable excipients is as stabilizers, antioxidants, osmotic adjusters, buffers, or pH adjusters, and may include starch, cellulose, glucose, lactose, sucrose, gelatin, corn, rice, flour, chalk, silica gel, magnesium stearate, sodium stearate, glycerol monostearate, sodium chloride, glycerol, propylene glycol, water, ethanol, and the like.

Suitable additives include physiologically biocompatible buffers (for example, tromethamine hydrochloride), chelating agents (for example, DTPA or DTPA-bisamide), or calcium chelating complexes (for example, calcium DTPA, CaNaDTPA-bisamide), or optionally calcium salts or sodium salts (for example, calcium chloride, calcium ascorbate, calcium gluconate, or calcium lactate).

The composition may further include at least one selected from among a stem cell and a growth factor.

The composition may be used as a wound dressing, an adhesive, a surgical/medical device, artificial skin, a bandage, a foam agent, a film, an anti-adhesion agent, and a graft, preferably a wound dressing.

Another aspect of the present invention provides a composition including a fiberized acellular dermal matrix and water, wherein 90% or more of the fiberized acellular dermal matrix has a major axis length of 100 μm to 2,000 μm and the composition is prepared without addition of a biocompatible polymer.

Next, the present invention will be described in more detail with reference to some examples. It should be understood that these examples are provided for illustration only and are not to be construed in any way as limiting the invention.

Example 1: Method of Preparing a Composition Using a Fiberized Acellular Dermal Matrix Derived from Human Skin tissue (homologous dermis derived from human) isolated from a cadaver and having a thickness of 0.5 mm or more was used in preparation of a fiberized acellular dermal matrix. The skin tissue was decellularized by a known method.

The acellular dermal matrix was pulverized into fine fibers using a cutting mill under conditions of a rotational speed of 500 rpm to 2,000 rpm and a sieve size of 500 μm to 1,000 μm.

The fiberized freeze-dried acellular dermal matrix was rehydrated by adding sterile distilled water in an amount three or more times the volume by weight of the fiberized freeze-dried acellular dermal matrix.

The rehydrated fiberized acellular dermal matrix was spread to a thickness of 0.1 mm or more on a sieve (mesh) (sieve size: 100 μm or more) in a water bath containing sterile distilled water, followed by shaking of the water bath or stirring with a magnetic bar to ensure even distribution of the fiberized acellular dermal matrix.

After the fiberized acellular dermal matrix was evenly distributed, the sieve (mesh) was raised to discharge the sterile distilled water therethrough and to filter out only a fiberized acellular dermal matrix having a major axis length of 100 μm or more. The fiberized acellular dermal matrix remaining on the sieve was subjected to freeze-drying to form a sheet. Here, freeze-drying may be performed with the fiberized acellular dermal matrix spread on the mesh.

A thickness of the sheet-type composition as a final product was controlled by adjusting the amount of the fiberized acellular dermal matrix spread on the mesh or by cutting the sheet-type composition to a desired thickness after drying.

Example 2: Comparison in Structure Between Acellular Dermal Matrices

FIG. 1 shows the structure of the fiberized acellular dermal matrix (A) used in the composition prepared in Example 1 and a non-fiberized acellular dermal matrix (B), as observed by optical microscopy.

The non-fiberized acellular dermal matrix (B) was prepared by subjecting an acellular dermal matrix having a thickness of 1 mm or less to decellularization, freeze-drying, and pulverization in the same manner as in preparation of the fiberized acellular dermal matrix (A) except that the acellular dermal matrix was pulverized into random shapes rather than into fine fibers.

The fiberized acellular dermal matrix (A) exhibited a network structure, that is, a structure composed of entangled fibers, and had a large surface area and a stable structural shape, as compared to the non-fiberized acellular dermal matrix (B).

Conversely, the non-fiberized acellular dermal matrix (B) was present in the form of near-spherical particles with a small surface area, making it difficult to form a structure composed of entangled particles.

Example 3: Comparison in Structure Between an Acellular Dermal Matrix Derived from Human and ADM According to the Present Invention It was confirmed that the composition using the fiberized acellular dermal matrix prepared in Example 1 has a similar tissue structure to an acellular dermal matrix derived from human skin.

FIG. 2 shows SEM images (×200) of the acellular dermal matrix derived from human skin (A) and the composition using the fiberized acellular dermal matrix prepared in Example 1 (B).

Experimental Example: Structural Stability

An experiment was conducted to determine whether the sheet-type composition according to the present invention can maintain a shape thereof without disentanglement after prolonged rehydration.

In FIG. 3, each of the sheets denoted by (0d), (1d), and (7d) is the sheet-type composition according to the present invention.

- Sheet (0d) of FIG. 3 represents the sheet-type composition on day 0 of rehydration.
- Sheet (1d) of FIG. 3 represents the sheet-type composition on day 1 of rehydration.

Sheet (7d) of FIG. 3 represents the sheet-type composition on day 7 of rehydration.

It was confirmed that, due to the network structure thereof as seen in FIG. 1, the sheet-type composition according to the present invention can maintain a shape thereof without disentanglement of the fiberized particles after prolonged rehydration.

As described above, the method of preparing a composition using a fiberized acellular dermal matrix according to the present invention can prevent heat-induced property changes in the composition by omitting addition of a biocompatible polymer, can reduce the number of preparation steps by eliminating the need for a process of dissolving the polymer in high-temperature water and mixing the dissolved polymer with the fiberized acellular dermal matrix and a process of heat treatment of the mixture of the fiberized acellular dermal matrix and the polymer, and can reduce preparation costs by eliminating the need for additional equipment and manpower for heat treatment.

In addition, since the fiberized acellular dermal matrix can form a network structure by spreading the composition on a mesh, the composition can be prepared in sheet form without addition of a biocompatible polymer.

The composition according to the present invention is soft due to omission of a polymer and thus can be easily applied to wounds in areas which make application of a conventional composition difficult due to the irregularity, size, or shape thereof.

In addition, since the composition according to the present invention has a network structure without addition of a polymer by using the fiberized acellular dermal matrix, that is, an acellular dermal matrix having a large major axis length, the composition can have high structural stability and can be prepared in the form of a sheet-type wound dressing to be uniformly applied to a wound site without flowing down therefrom, thereby ensuring improved therapeutic effects.

In particular, the composition according to the present invention has a very similar structure to a dermal matrix at a wound site by omitting addition of a polymer, and thus has good properties in terms of bioadhesion and in-vivo integrity, and maintains a moist environment well, thereby providing good therapeutic effects.

In addition, the composition according to the present invention has good shape retention during specialized procedures due to high stability after prolonged rehydration, and can be prepared into sheets having various widths, lengths, and thicknesses depending on the type of wound site or the nature of surgery, thereby ensuring improved treatment of wounds.

Although some embodiments have been disclosed herein, it will be apparent to those skilled in the art that the present invention is not limited thereto and various modifications, changes, and alterations can be made without departing from the spirit and scope of the invention.

The invention claimed is:

1. A method of preparing a composition using a fiberized acellular dermal matrix, comprising:

(a) preparing a fiberized acellular dermal matrix by pulverizing an acellular dermal matrix, the pulverization being carried out using a cutting mill under conditions of a rotational speed of 500 rpm to 2,000 rpm and a sieve size of 500 μm to 1,000 μm;

(b) preparing a rehydrated fiberized acellular dermal matrix by adding distilled water to the fiberized acellular dermal matrix;

(c) separating the rehydrated fiberized acellular dermal matrix based on a major axis length thereof; and (d) drying the separated rehydrated fiberized acellular dermal matrix, wherein the composition is prepared without addition of a biocompatible polymer.

2. The method according to claim 1, wherein the step (c) comprises spreading the rehydrated fiberized acellular dermal matrix on a mesh, followed by discharging a fiberized acellular dermal matrix having a major axis length shorter than a sieve size of the mesh through the mesh along with water.

3. The method according to claim 2, wherein the step (d) comprises drying the rehydrated fiberized acellular dermal matrix remaining on the mesh.

4. The method according to claim 2, further comprising: before the step (c), adding water to the mesh in an amount three or more times a volume by weight of the rehydrated fiberized acellular dermal matrix such that the fiberized acellular dermal matrix is evenly distributed.

5. The method according to claim 2, wherein the step (c) comprises spreading the rehydrated fiberized acellular dermal matrix on the mesh, followed by discharging a fiberized acellular dermal matrix having a major axis length of less than 100 μm through the mesh along with water.

6. The method according to claim 5, wherein the step (c) comprises separating the fiberized acellular dermal matrix such that 90% or more of the separated fiberized acellular dermal matrix has a major axis length of 100 μm to 2,000 μm.

7. The method according to claim 5, wherein the step (c) comprises separating the fiberized acellular dermal matrix such that 50% to 90% or more of the separated fiberized acellular dermal matrix has a major axis length of 600 μm to 800 μm.

8. The method according to claim 1, further comprising: processing the dried fiberized acellular dermal matrix into sheet form.

9. The method according to claim 1, further comprising: crosslinking the fiberized acellular dermal matrix.

* * * * *